United States Patent [19]

Link et al.

[11] Patent Number: 5,003,831
[45] Date of Patent: Apr. 2, 1991

[54] PROCESS FOR MONITORING A DEVICE FOR AUTOMATICALLY DETECTING AND EVALUATING SURFACE CRACKS

[75] Inventors: Rainer Link, Kerpen-Horrem; Wolfgang Nuding, Troisdorf, both of Fed. Rep. of Germany

[73] Assignee: Isotopenforschung Dr. Sauerwein GmbH, Haan, Fed. Rep. of Germany

[21] Appl. No.: 458,586

[22] Filed: Dec. 29, 1989

[30] Foreign Application Priority Data

Mar. 10, 1989 [DE] Fed. Rep. of Germany ....... 3907732

[51] Int. Cl.$^5$ ............................................. H04N 7/18
[52] U.S. Cl. ................................................. 73/865.9
[58] Field of Search ...................... 73/104, 1 R, 865.9; 358/106, 101; 324/216, 202

[56] References Cited

FOREIGN PATENT DOCUMENTS 0226853 12/1984 Japan ................................. 324/216
0052453 3/1987 Japan ................................. 324/216
0150662 6/1988 Japan ................................. 324/216

Primary Examiner—Robert Raevis
Attorney, Agent, or Firm—Toren, McGeady & Associates

[57] ABSTRACT

In a process for monitoring a device for automatically detecting and evaluating surface cracks by means of magnetic powder or the dye penetration process comprising an image pick-up camera and a digital image processing and control unit, a typical defect pattern is projected by means of a projector onto the surface of the article to be examined in the pick-up region of the image pick-up camera and registered, and a defect indication is triggered if the device ceases to operate reliably.

10 Claims, 1 Drawing Sheet

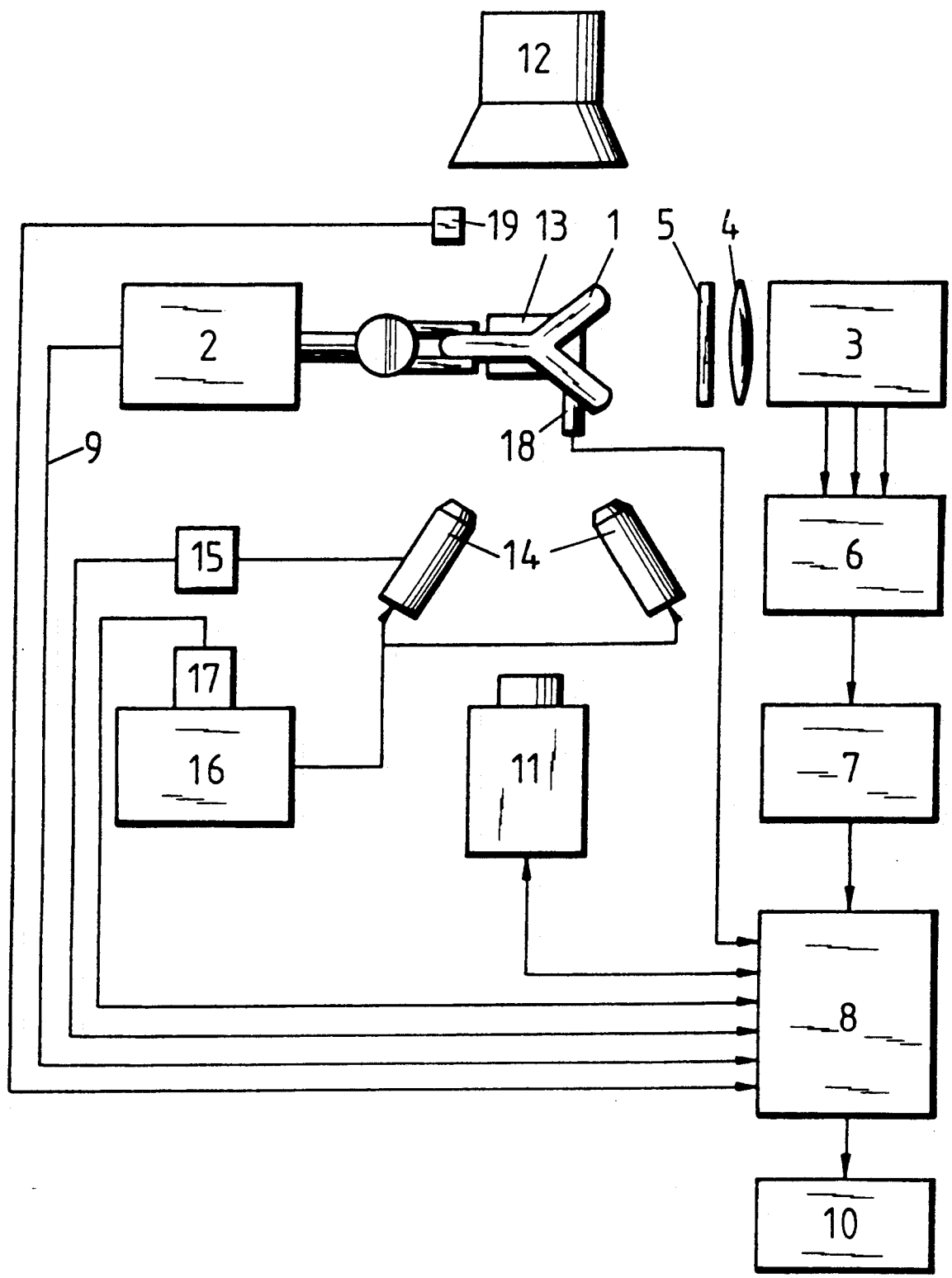

PROCESS FOR MONITORING A DEVICE FOR AUTOMATICALLY DETECTING AND EVALUATING SURFACE CRACKS

TECHNICAL FIELD OF THE INVENTION

The invention relates to a process for monitoring a device for automatically detecting and evaluating surface cracks, in particular by means of magnetic powder or by the dye penetration method, in which a sorting report is triggered with the aid of an image pick-up device and a digital image processing and control unit.

BACKGROUND OF THE INVENTION AND PRIOR ART

A device of this kind is described in German patent publication No. 34 40 471. In this device a robot brings the article to be examined from a conveyor into a strong magnetic field. A crack in the surface gives rise to a particularly strong magnetic field on the surface in the region of the crack. If a solution which contains a magnetic powder is applied to the magnetized article to be examined the magnetic particles concentrate on the crack and are held there while the magnetic powder particles are washed away from the undamaged parts of the surface by the solution. On irradiation by means of a UV Lamp the crack-free surface only glows diffusely while the magnetic powder, which has a fluorescing agent added to it, gives a sharp crack indication in the region of the crack. This crack indication is registered by means of an image pick-up camera and is input into the digital image processing and control unit, where it triggers a sorting report.

To ensure reliable automatic testing a device such as this must be checked periodically. For this purpose it is known to provide a control body with defect patterns which can only just be detected reliably. This control body serves to demonstrate the sensitivity and to test the performance of the entire system. It is also possible to use test workpieces having natural defects.

For continuous monitoring of an automatic device for detecting and evaluating surface cracks a test body would have to be repeatedly passed through the device and then again demagnetised and cleaned. Practical experience however has shown that cracks, like artificial defects, grow with time and that the intensity of the crack indication becomes weaker after even a few test cycles, so that as time goes on monitoring with repeatedly used test bodies becomes ineffective.

Furthermore introducing test bodies or defective parts into an automatic system causes problems as there is always the danger that the test body or the defective part may not be removed again and therefore cause damage. Moreover test bodies having artificial defect patterns are expensive, which is of particular significance if they can only be used a few times.

OBJECT OF THE INVENTION

It is therefore an object of the invention to provide a monitoring process for devices operating with an image pick-up device, for example a camera, which avoids the use of test bodies and can therefore be carried out simply and reliably and requires little outlay on apparatus.

SUMMARY OF THE INVENTION

To this end, according to the invention, in a process of the kind mentioned in the introduction a defect pattern typical of that which is to be detected is projected by means of a projector on to the surface of the article to be examined in the pick-up region of the image pick-up device in order to generate a defect indication. With the process according to the invention is in no longer necessary to introduce defective parts or test bodies so that there is no longer the risk of such defective parts or test bodies not being passed out again in some unfortunate circumstances.

The monitoring can be carried out without particular expense at short intervals, which result in greater reliability. It is no longer necessary to repeatedly use defective parts or test bodies, which can give rise to problems for physical reasons. Uneconomical manufacture of a large number of test bodies with defect patterns, which in addition is technically difficult, is likewise dispensed with.

The process according to the invention can be carried out without difficulty periodically after a given number of articles has been examined, and it is suitable for all devices in which cracks are detected by an image pick-up device and the crack image is converted into signals.

Additional control parameters can be used to further increase the reliability of the process and to monitor the quality of the testing process performed with the device for automatically detecting and evaluating surface cracks. This involves measuring the magnetization of the article to be examined and comparing it with an intended value. In doing this, magnetization is preferably determined by measuring the tangential field strength.

Monitoring the solution containing the magnetic powder and/or fluorescent pigment particles can also be carried out continuously or periodically. Types of apparatus used in chemical processes are suitable for this.

Since uniform wetting of the surface to be examined with the solution containing the magnetic powder and/or fluorescent pigment particles is also important for the quality of the control process, this can also be monitored, e.g. by means of flow indicators.

The detection of defects is highly dependent on the correct illumination by means of the UV lamp. It is therefore important to monitor the light from the UV lamp continuously or periodically. Known sensors can be used for this purpose.

Since the digital image processing and control unit triggers a sorting result at a threshold value produced by cracks, the same unit can also be used to compare the measured test and/or monitoring values with corresponding intended values in order to trigger a defect indication in the event of an impermissible difference.

The invention will now be explained with reference to an exemplary embodiment shown in the drawing.

DETAILED DESCRIPTION OF A PREFERRED EMBODIMENT OF THE INVENTION

A workpiece 1 is brought into the neighbourhood of a magnetizing device 13 by means of a manipulator 2. Here the article or workpiece 1 is sprayed by means of spray nozzles 14 with a solution containing a magnetic powder and/or fluorescent pigment particles. The magnetic powder is retained by magnetization in the region of the cracks extending to the surface of the workpiece and is rendered visible through irradiation by means of a UV lamp 12.

The image of the workpiece 1, with any cracks that have been made visible, reaches a colour television camera 3 by way of an optional filter 5 and a lens 4 which converts the image into electronic signals which are supplied to a colour mixing unit 6 and an analog-digital converter 7 of a digital image processing and control unit 8. The digitalized image is processed in the digital image processing and control unit 8 so that a binary image of any cracks present is generated, and if it exceeds a predetermined threshold value a sorting result is triggered. This sorting result from the digital image processing and control unit 8 reaches the manipulator 2 by way of a control line 9, and gives it the command to separate out the workpiece 1.

In order to monitor the operation of the device from time to time a defeat image is projected by means of a projector 11 on to the workpiece 1 and picked up by the colour television camera 3. If this defect image is detected, a sorting result is triggered in the digital image processing and control unit, which indicates that the device is operating correctly.

Furthermore, a flow indicator 15 is arranged on the spray nozzles 14 which serves to monitor the uniform wetting of the workpiece 1 with the solution containing the magnetic powder and/or fluorescent pigment particles. Moreover, an analytical device 17 is arranged on a supply tank 16 for the solution, which automatically monitors the composition of the soluion. Such analytical devices are known in chemical process engineering.

In addition a magnetization sensor 18 measures either periodically or continuously the tangential field strength which is a measure of the magnetization of the workpiece 1.

Finally, a UV light sensor 19 is arranged in the irradiation region of the UV lamp 12 so that the constancy of the UV lamp can also be monitored. The projector 11, the flow indicator 15, the analytical device 17, the magnetization sensor 18 and the UV light sensor 19 are connected to the digital image processing and control unit 8 in which the measured test and/or monitoring values are compared with corresponding intended values so that in the event of an impermissible variation a defect indication is triggered.

With the process according to the invention a fully automatic monitoring of a device of the kind mentioned in the introduction can thus be carried out which leads to immediate shut-down if there are defects in the device.

What is claimed is:

1. A process for monitoring a device for automatically detecting and evaluating surface cracks in articles by means of magnetic powder or by a dye penetration process in which a sorting result is triggered by means of an image pick-up device and a digital image processing and control unit, comprising the steps of projecting a typical defect pattern by means of a projector onto a surface of an article to be examined in a pick-up region of the image pick-up device, and establishing a defect indication of the defect pattern.

2. A process according to claim 1, including the step of projecting the defect pattern periodically or on demand.

3. A process according to claim 1, including the step of measuring and comparing magnetization of the article to be examined with an intended value.

4. A process according to claim 3, including the step of determining the magnetization by measuring the tangentail field strength.

5. A process according to claim 1, including the step of checking composition of a solution containing the magnetic powder and/or fluorescent pigment particles.

6. A process according to claim 1, including the step of checking uniform wetting of the article to be examined with a solution containing the magnetic powder and/or fluorescent pigment particles.

7. A process according to claim 6, including the step of monitoring the uniform wetting by at least one flow indicatior.

8. A process according to claim 1, including the step of checking the light of a UV lamp irradiating the surface of the article to be examined.

9. A process according to claim 8, including the step of periodically checking the constancy of the light of the UV lamp.

10. A process according to claim 1, including the steps of supplying measured test and/or monitoring values to the digital image processing and control unit and comparing with intended values, and triggering a defect indication if there is at least one impermissible difference.

* * * * *